United States Patent
Shea et al.

(10) Patent No.: US 11,375,970 B2
(45) Date of Patent: *Jul. 5, 2022

(54) INTEGRATED HELICAL FAN-BEAM COMPUTED TOMOGRAPHY IN IMAGE-GUIDED RADIATION TREATMENT DEVICE

(71) Applicant: Accuray, Inc., Sunnyvale, CA (US)

(72) Inventors: Jacob Shea, Madison, WI (US); Daniel Gagnon, Twinsburg, OH (US); Eric Schnarr, McFarland, WI (US); Edward Henry Chao, Sauk City, WI (US); Petr Jordan, Emerald Hills, CA (US); Calvin R. Maurer, Jr., San Jose, CA (US)

(73) Assignee: Accuray, Inc., Sunnyvale, CA (US)

(*) Notice: Subject to any disclaimer, the term of this patent is extended or adjusted under 35 U.S.C. 154(b) by 146 days.

This patent is subject to a terminal disclaimer.

(21) Appl. No.: 16/694,161

(22) Filed: Nov. 25, 2019

(65) Prior Publication Data
US 2020/0171328 A1 Jun. 4, 2020

Related U.S. Application Data

(60) Provisional application No. 62/878,364, filed on Jul. 25, 2019, provisional application No. 62/843,796, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
CPC .. A61B 6/00; A61B 6/02; A61B 6/027; A61B 6/03; A61B 6/04; A61B 6/0487;
(Continued)

(56) References Cited

U.S. PATENT DOCUMENTS 4,190,773 A  2/1980 Braden et al.
5,615,279 A  3/1997 Yoshioka et al.
(Continued)

FOREIGN PATENT DOCUMENTS

DE  10 2006 007058 A1  7/2007
EP     1062914 A1  12/2000
(Continued)

OTHER PUBLICATIONS

Zhu, et al. Noise suppression in scatter correction for cone-beam CT, American Association of Physicists in Medicine, 2009, pp. 741-752, vol. 36, No. 3.
(Continued)

*Primary Examiner* — Anastasia Midkiff
(74) *Attorney, Agent, or Firm* — Calfee, Halter & Griswold LLP

(57) ABSTRACT

A radiotherapy delivery device is provided. The device includes a source of therapeutic radiation and a first detector positioned to receive radiation from the source of therapeutic radiation. The device also includes a source of imaging radiation and a second detector positioned to receive radiation from the source of imaging radiation. A collimator assembly is positioned relative to the second source of radiation to selectively control a shape of a radiation beam emitted by the second radiation source to selectively expose part or the whole of the second radiation detector. A reconstruction processor can be operatively coupled to the detector and configured to generate patient images based on radiation received by the second detector from the second
(Continued)

source of radiation. The device is configured to move from one imaging geometry to another using all or part of the second detector.

19 Claims, 6 Drawing Sheets

Related U.S. Application Data filed on May 6, 2019, provisional application No. 62/836,357, filed on Apr. 19, 2019, provisional application No. 62/836,352, filed on Apr. 19, 2019, provisional application No. 62/821,116, filed on Mar. 20, 2019, provisional application No. 62/813,335, filed on Mar. 4, 2019, provisional application No. 62/801,260, filed on Feb. 5, 2019, provisional application No. 62/800,287, filed on Feb. 1, 2019, provisional application No. 62/796,831, filed on Jan. 25, 2019, provisional application No. 62/773,712, filed on Nov. 30, 2018, provisional application No. 62/773,700, filed on Nov. 30, 2018.

(51) Int. Cl.

| | | |
|---|---|---|
| *A61B 6/03* | (2006.01) | |
| *A61B 6/06* | (2006.01) | |
| *A61B 6/02* | (2006.01) | |
| *A61N 5/10* | (2006.01) | |
| *A61B 6/08* | (2006.01) | |
| *G06T 7/30* | (2017.01) | |
| *A61B 5/055* | (2006.01) | |
| *A61B 6/04* | (2006.01) | |

(52) U.S. Cl.
CPC ............ *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(58) Field of Classification Search
CPC ......... A61B 6/06; A61B 6/405; A61B 6/4078; A61B 6/44; A61B 6/4429; A61B 6/48; A61B 6/483; A61B 6/486; A61B 6/52; A61B 6/5205; A61B 6/5211; A61B 6/5223; A61B 6/5258; A61B 6/5282; A61N 5/10; A61N 5/103; A61N 5/1042; A61N 5/1045; A61N 5/1047; A61N 5/1048; A61N 5/1064; A61N 5/1065; A61N 5/1067; A61N 5/1081; G21K 1/00; G21K 1/02; G21K 1/04; G21K 1/1043; G21K 1/1046; G21K 1/10; G21K 5/04; G21K 5/10; G21K 2207/00; G21K 2207/005; G06T 7/30; G06T 11/005; G06T 11/008; G06T 2207/10081; G06T 2210/41; G06T 2211/482; G06T 2211/424; G06T 2211/428

See application file for complete search history.

(56) References Cited

U.S. PATENT DOCUMENTS

| | | | |
|---|---|---|---|
| 6,233,478 | B1 | 5/2001 | Liu |
| 6,307,909 | B1 | 10/2001 | Flohr et al. |
| 7,050,528 | B2 | 5/2006 | Chen |
| 7,660,380 | B2 | 2/2010 | Boese et al. |
| 8,116,430 | B1 | 2/2012 | Shapiro et al. |
| 8,467,497 | B2* | 6/2013 | Lu .................. A61N 5/1049 378/65 |
| 8,588,363 | B2 | 11/2013 | Flohr |
| 9,400,332 | B2 | 7/2016 | Star-Lack et al. |
| 2003/0007601 | A1 | 1/2003 | Jaffray et al. |
| 2003/0076927 | A1 | 4/2003 | Shigeyuki et al. |
| 2004/0091079 | A1 | 5/2004 | Zapalac |
| 2004/0102688 | A1 | 5/2004 | Walker et al. |
| 2004/0202360 | A1 | 10/2004 | Besson |
| 2005/0053188 | A1 | 3/2005 | Gohno |
| 2005/0251029 | A1 | 11/2005 | Khamene et al. |
| 2006/0109954 | A1 | 5/2006 | Gohno |
| 2006/0262894 | A1 | 11/2006 | Bernhadt et al. |
| 2007/0127621 | A1 | 6/2007 | Grass et al. |
| 2007/0189444 | A1 | 8/2007 | Van Steven-Daal et al. |
| 2008/0112532 | A1 | 5/2008 | Schlomka et al. |
| 2009/0080603 | A1 | 3/2009 | Shukla et al. |
| 2009/0135994 | A1 | 5/2009 | Yu et al. |
| 2009/0161826 | A1* | 6/2009 | Gertner ................ A61N 5/1017 378/65 |
| 2009/0225932 | A1 | 9/2009 | Zhu et al. |
| 2009/0283682 | A1 | 11/2009 | Star-Lack et al. |
| 2010/0046819 | A1 | 2/2010 | Noo et al. |
| 2010/0142791 | A1 | 6/2010 | Tsuji |
| 2010/0208964 | A1 | 8/2010 | Wiegert et al. |
| 2011/0142312 | A1 | 6/2011 | Toth et al. |
| 2012/0014582 | A1 | 1/2012 | Schaefer et al. |
| 2012/0207370 | A1 | 8/2012 | Fahimian et al. |
| 2012/0263360 | A1 | 10/2012 | Zhu et al. |
| 2012/0294504 | A1 | 11/2012 | Kyriakou |
| 2013/0101082 | A1 | 4/2013 | Jordan et al. |
| 2013/0294570 | A1 | 11/2013 | Hansis |
| 2014/0018671 | A1 | 1/2014 | Li et al. |
| 2014/0086383 | A1 | 3/2014 | Huwer et al. |
| 2015/0297165 | A1 | 10/2015 | Tanaka et al. |
| 2015/0305696 | A1 | 10/2015 | Tamakawa et al. |
| 2016/0016009 | A1 | 1/2016 | Manzke et al. |
| 2016/0120486 | A1 | 5/2016 | Goto et al. |
| 2016/0262709 | A1 | 9/2016 | Siewerdsen et al. |
| 2017/0000428 | A1 | 1/2017 | Goto |
| 2017/0197098 | A1 | 7/2017 | Hirasawa et al. |
| 2017/0205360 | A1 | 7/2017 | Cinquin et al. |
| 2017/0278277 | A1 | 9/2017 | Morf et al. |
| 2017/0332982 | A1 | 11/2017 | Koehler et al. |
| 2018/0028143 | A1 | 2/2018 | Wiggers et al. |
| 2018/0070894 | A1 | 3/2018 | Osaki et al. |
| 2018/0192978 | A1 | 7/2018 | Naylor |
| 2018/0345042 | A1 | 12/2018 | Voronenko et al. |
| 2020/0121267 | A1 | 4/2020 | Deutschmann |
| 2020/0170585 | A1* | 6/2020 | Yu .................. A61B 6/027 |
| 2020/0170590 | A1* | 6/2020 | Gagnon .............. A61B 6/5282 |
| 2020/0170591 | A1* | 6/2020 | Gagnon .............. A61B 6/488 |
| 2020/0170592 | A1* | 6/2020 | Bai .................. A61B 6/027 |
| 2020/0170596 | A1* | 6/2020 | Yu .................. A61B 6/5282 |
| 2020/0170598 | A1* | 6/2020 | Shea .................. A61B 6/50 |
| 2020/0170600 | A1* | 6/2020 | Yu .................. A61B 6/488 |

(56) References Cited

U.S. PATENT DOCUMENTS

| | | | | |
|---|---|---|---|---|
| 2020/0170601 | A1* | 6/2020 | Gagnon | A61B 6/06 |
| 2020/0170607 | A1* | 6/2020 | Yu | A61N 5/1081 |
| 2021/0165122 | A1 | 6/2021 | Morton | |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015103184 A1 | 7/2015 |
| WO | 2018/156968 A1 | 8/2018 |
| WO | 2018/183748 A1 | 10/2018 |

OTHER PUBLICATIONS

Office Action from U.S. Appl. No. 16/694,145 dated Mar. 17, 2021, 10 pages.
Office Action from U.S. Appl. No. 16/694,190 dated Mar. 26, 2021, 9 pages.
Notice of Allowance from U.S. Appl. No. 16/694,190 dated Jun. 23, 2021, 8 pages.
Office Action from U.S. Appl. No. 16/694,230 dated Apr. 1, 2021, 6 pages.
Office Action from U.S. Appl. No. 16/694,202 dated Apr. 9, 2021, 12 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Restriction Requirement from U.S. Appl. No. 16/694,210 dated Jun. 10, 2021, 6 pages.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging, Physics in Medicine and Biology, pp. 6729-6748, vol. 51.
Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Schäfer, et al., FBP and BPF reconstruction methods for circular X-ray tomography with off-center detector, Med. Phys., Jul. 2011, pp. S85-S94, vol. 38, No. 7.

Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Siewerdsen, et al., A simple, direct method for x-ray scatter estimation and correction in digital radiography and cone-beam CT, Med. Phys., Jan. 2006, pp. 187-197, vol. 33, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
International Search Report and Written Opinion from PCT/US2019/063080 dated Mar. 16, 2020.
International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11 , Radiology, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Anas, et al., High-quality 3D correction of ring and radiant artifacts in flat panel detector-based cone beam volume CT Imaging, Phys. Med. Biol., 2011, pp. 6495-6519, vol. 56.
Bootsma, et al., Spatial frequency spectrum of the x-ray scatter distribution in CBCT projections, Med. Phys., Nov. 2013, pp. 111901-1-111901-15, vol. 40, No. 11.

(56) References Cited

OTHER PUBLICATIONS

International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correction methods in cone beam CT. Part 2: Scatter estimation approaches, Med. Phys. Sep. 2011, pp. 5186-5199, vol. 38, No. 9.
Yang, et al., Scattering estimation for cone-Beam CT Using Local Measurement Based on Compressed Sensing, IEEE transactions on Nuclear Science, Mar. 2018, pp. 941-949, vol. 65, No. 3.

* cited by examiner

INTEGRATED HELICAL FAN-BEAM COMPUTED TOMOGRAPHY IN IMAGE-GUIDED RADIATION TREATMENT DEVICE

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled "MULTI-PASS COMPUTED TOMOGRAPHY SCANS FOR IMPROVED WORKFLOW AND PERFORMANCE;" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMPROVING SCATTER ESTIMATION AND CORRECTION IN IMAGING." The contents of all above-identified patent application(s) and patent(s) are fully incorporated herein by reference.

FIELD OF THE INVENTION

Aspects of the disclosed technology relate to image-guided radiation treatment (IGRT), and, more particularly, to a system and method using a low energy (e.g., kilovolt x-ray) radiation source for high-quality imaging, including helical fan-beam computed tomography for use in IGRT.

BACKGROUND

Radiotherapy is often carried out by directing a high-energy beam of x-rays (e.g., at an energy level in the megavoltage range) toward a tumor or other region of interest within a patient. The goal of the treatment is to focus the high-energy x-ray beam on the region of interest, while minimizing the exposure of surrounding tissue. Medical imaging technology can be used in connection with the radiotherapy procedure. So-called IGRT makes use of medical imaging technology, such as computed tomography (CT), to collect images of a patient for use in image-based pre-delivery steps, which can include treatment planning. Image acquisition can also be used to confirm that therapeutic radiation beams are correctly directed to and treating the region of interest.

BRIEF SUMMARY

In one embodiment, a radiotherapy delivery device includes a rotatable gantry positioned at least partially around a patient support, a first radiation source coupled to the rotatable gantry system, the first radiation source configured for therapeutic radiation, a second radiation source coupled to the rotatable gantry system, the second radiation source configured for imaging radiation, wherein the second radiation source comprises an energy level less than the first radiation source, a radiation detector coupled to the rotatable gantry system and positioned to receive radiation from the second radiation source, and a collimator assembly positioned relative to the second radiation source to selectively control a shape of a radiation beam emitted by the second radiation source to selectively expose the radiation detector to the radiation beam during a helical scan.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

Figure 1:
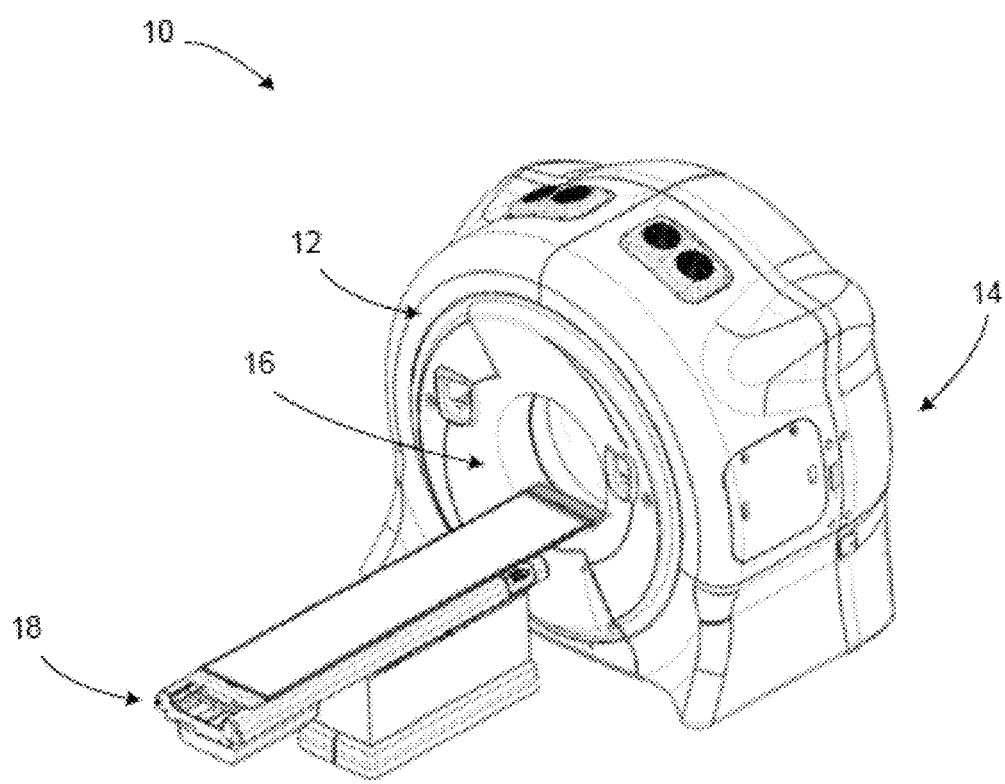
FIG. 1 is a perspective view of an exemplary radiotherapy delivery device in accordance with one aspect of the disclosed technology.

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to a radiotherapy delivery device and method that make use of an integrated low-energy radiation source for CT for use in conjunction with or as part of IGRT. In particular, for example, a radiotherapy delivery device and method can combine a low-energy collimated radiation source for imaging in a gantry using rotational (e.g., helical or step-and-shoot) image acquisition along with a high-energy radiation source for imaging and/or therapeutic treatment. In one embodiment, the low-energy radiation source is a kilovolt (kV) radiation source as part of a CT system and the high-energy radiation source for therapeutic treatment is a megavolt (MV) radiation source. Embodiments below mentioning kV radiation sources may also utilize other low-energy radiation sources.

The low-energy radiation source (e.g., kV) can produce higher quality images than via use of the high-energy (e.g., MV) for imaging. Images generated with kV energy have better tissue contrast than with MV energy. High quality volume imaging is needed for visualization of targets and organs-at-risk (OARS), for adaptive therapy monitoring and for treatment planning/re-planning. In some embodiments, the kV imaging system can also be used for motion tracking and/or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc. In some embodiments, the source of imaging radiation utilizes a collimated fan beam from a kV radiation source.

There are many determinants of image quality (e.g., X-ray source focal spot size, detector dynamic range, etc.). For example, a limitation of kV cone beam computed tomography (CBCT) image quality can be scatter. Various approaches can be used to reduce scatter. One approach is to use an anti-scatter grid (which collimates the scatter). However, it can be problematic to implement a scatter grid on a kV imaging system, including for motion tracking and correction. Another is to attempt to correct for scatter in the reconstruction process, including advanced reconstruction algorithms (e.g., software-based scatter correction).

In accordance with various embodiments, the radiotherapy device collimates the low-energy radiation source, including, for example, into a cone beam or a fan beam using, for example, a collimator (which may include or be a part of a beamformer) to limit the beam. In one embodiment, the collimated beam can be combined with a gantry that continuously rotates while the patient moves resulting in a helical image acquisition.

In some embodiments, the fan beam is a fan beam or a "thick-fan" kV beam collimation. A thick-fan beam may be a beam that exposes more rows of a multi-row radiation detector than a fan beam, but still avoids the artifacts associated with a cone beam (CB), as described in more detail below. Relative to conventional in-treatment imaging systems, such as, for example, CBCT, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high kV frame rates, and/or sparse data reconstruction techniques, to provide kV CT imaging on a radiation therapy delivery platform. Flat-panel detectors (with various row/slice sizes, configurations, dynamic range, etc.), scan pitch, and/or dynamic collimation are additional features in various embodiments, including to selectively expose portions of the detector, as discussed in detail below. In particular, image quality can be improved by using an adjustable collimator on the low-energy imaging radiation source by the reduction of scatter. Another advantage is the reduction of radiation exposure. It will be appreciated that such an implementation can provide reduced scatter and improved scatter estimation to enable kV images of higher quality than conventional systems, such as, for example, CBCT.

The radiotherapy delivery device and method can provide selective and variable collimation of a kV radiation source, including a fan-beam geometry that exposes less than the entire active area of an associated radiation detector (e.g., a radiation detector positioned to receive radiation from the kV radiation source). The disclosed radiotherapy device and method can allow for selectively controlling a beam from a source of radiation, including the ability to adjust the beam geometry, selectively exposing all or part of an associated detector. Exposing only a primary region of the detector to direct radiation allows shadowed regions of the detector to receive only scatter. In some embodiments, scatter measurements in the shadow region (and in some embodiments measurements in the penumbra region) of the detector can be used to estimate scatter in the primary region of the detector receiving projection data.

The radiotherapy delivery device and method can provide selective and variable detector readout areas and ranges, including adjusting the detector readout range to limit the active area of the detector for improved readout speed. For example, less than the available shadow region data may be read and used for scatter estimation. Combining selective readout with beamforming (collimating) allows for various optimizations of scatter fitting techniques.

Figure 2:
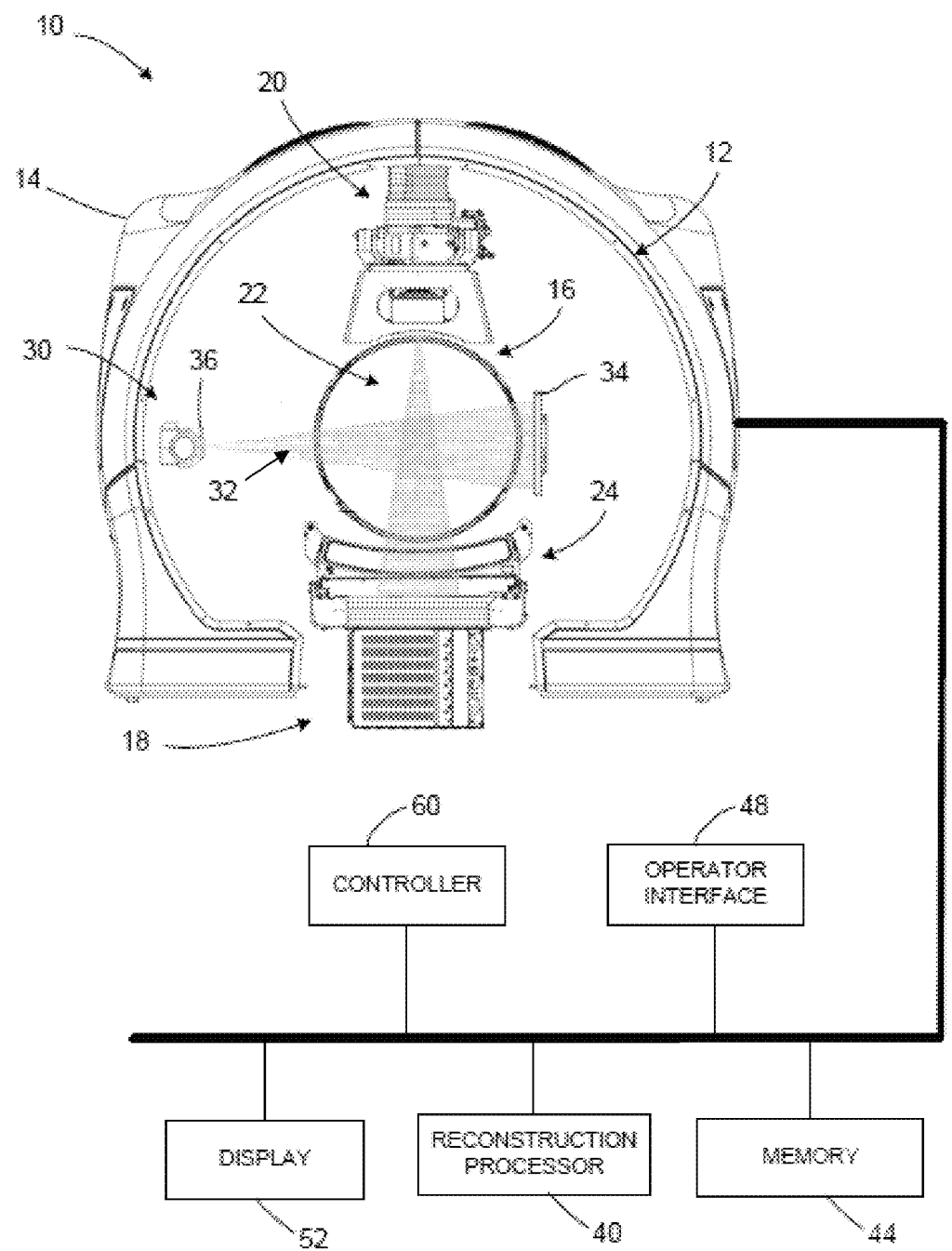
FIG. 2 is a diagrammatic illustration of an exemplary radiotherapy delivery device in accordance with one aspect of the disclosed technology.

With reference to FIG. 1 and FIG. 2, a radiotherapy device 10 is provided. It will be appreciated that the radiotherapy device 10 can be used for a variety of applications, including, but not limited to, image-guided radiation treatment or therapy (IGRT). The radiotherapy device 10 includes a rotatable gantry system, referred to as gantry 12, supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with a one embodiment, the rotatable gantry 12 is configured as a slip ring gantry to provide continuous rotation of an imaging radiation source and an associated radiation detector while providing sufficient bandwidth for the high-quality imaging data received by the detector. A slip-ring gantry can eliminate gantry rotations in alternating directions in order to wind and unwind cables carrying the power and signals associated with the device. As is discussed more fully below, such a configuration will allow for continuous helical (e.g., fan-beam, cone-beam, etc.) computed tomography, even when integrated into an IGRT system. As mentioned above, a major issue with single rotation CBCT is insufficient sampling on all slices except for the central slice (the one containing the rotation). This can be overcome by helical trajectory cone-beam imaging.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. In some embodiments, the patient support can also be moved in a limited range up and down, left and right once it is in the bore 16 to adjust the patient position for optimal treatment.

As shown in FIG. 2, the radiotherapy device 10 includes a first source of radiation 20 coupled to or otherwise supported by the rotatable gantry 12. In accordance with one embodiment, the first source of radiation 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation without departing from the scope of the disclosed technology. In one embodiment, the first source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the first source of radiation 20 has a higher energy level (peak and/or average, etc.) than the second source of radiation 30.

The imaging system, described in detail below, comprises a second source of radiation 30, which may be an independent x-ray imaging source producing relatively low intensity and lower energy imaging radiation. In one embodiment, the second source of radiation 30 is an x-ray source, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments.

It will be further appreciated that the first source of radiation 20 can emit one or more beams of radiation (indicated generally by 22) toward a region-of-interest (ROI) within a patient supported on the patient support 18. The first source of radiation can emit one or more beams of radiation in accordance with a treatment plan. It also will be appreciated that the treatment plan can include detailed parameters regarding source angular position, beam geometry, beam intensity, modulation, exposure, and the like.

In one embodiment, the first source of radiation 20 is a LINAC producing therapeutic radiation (e.g., MV) and the imaging system comprises an independent second source of radiation 30 producing relatively low intensity and lower energy imaging radiation (e.g., kV). In other embodiments, the first source of radiation 20 could be a radioisotope, such as, for example, Co-60, which can generally have energy >1 MeV. The first source of radiation 20 can emit one or more beams of radiation (indicated generally by 22) toward a region-of-interest (ROI) within a patient supported on the patient support 18 in accordance with a treatment plan.

As discussed in detail below, sources of radiation 20, 30 may be used in conjunction with one another to provide higher quality and better utilized images. In other embodiments, at least one additional radiation source can be coupled to the rotatable gantry 12 and operated to acquire projection data at a peak photon energy distinct from the peak photon energies of sources of radiation 20, 30.

Although FIGS. 1 and 2 depict a radiotherapy device 10 with a radiation source 20 mounted to a ring gantry 12, other embodiments may include other types rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

First detector 24 can be coupled to or otherwise supported by the rotatable gantry 12 and positioned to receive radiation 22 from the first source of radiation 20. The first detector 24 can detect or otherwise measure the amount of radiation not attenuated and therefore infer what was in fact attenuated by the patient or associated patient ROI (by comparison to what was initially generated). The first detector 24 can detect or otherwise collect attenuation data from different angles as the first radiation source 20 rotates around and emits radiation toward the patient. The collected attenuation data can be processed and reconstructed into one or more images of the patient's body.

The imaging system integrated within the radiotherapy device 10 can provide current images that are used to set up (e.g., align and/or register), plan, and/or guide the radiation delivery procedure (treatment). Typical set-up is accomplished by comparing current (in-treatment) images to pre-treatment image information. Pre-treatment image information may comprise, for example, CT data, CBCT data, magnetic resonance imaging (MRI) data, positron emission tomography (PET) data or 3D rotational angiography (3DRA) data, and/or any information obtained from these or other imaging modalities. In some embodiments, the imaging system can track in-treatment patient, target, or ROI motion.

Conventional in-treatment images typically comprise CBCT or two-dimensional images (typically x-ray). X-rays can be acquired at one or more different points of view (e.g., stereoscopic x-ray images), which can be compared with two-dimensional digitally reconstructed radiographs (DRRs) derived from the three-dimensional pre-treatment image information. CBCT can directly construct a 3D volumetric image from 2D projections of the target volume. As is known in the art, CBCT has the ability to form a 3D image volume from a single gantry rotation about the target volume with a more isotropic spatial resolution. However, scattering noise and artifacts are a significant problem for CBCT systems, limiting image quality. As can be appreciated, these and other conventional radiotherapy in-treatment imaging systems lack the ability to produce high-quality images, which can be similar to that of the pre-treatment images and suitable for image-based pre-delivery steps, including real-time treatment planning.

As shown in FIG. 2, the imaging system integrated within the radiotherapy device 10 includes a second source of radiation 30 coupled to or otherwise supported by the rotatable gantry 12. As discussed above, the second source of radiation 30 can be configured as a source of imaging radiation (e.g., kV) for high-quality in-treatment images (indicated generally as 32) having an energy level less than the first source 20 of therapeutic radiation.

A second detector 34 (e.g., two-dimensional flat detector or curved detector) can be coupled to or otherwise supported by the rotatable gantry 12. The second detector 34 is positioned to receive radiation from the second source of radiation 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the second radiation source 30 rotates around and emits radiation toward the patient.

A collimator or beamformer assembly (indicated generally as 36) is positioned relative to the second source of radiation 30 to selectively control and adjust a shape of a radiation beam 32 emitted by the second radiation source 30 to selectively expose a portion or region of the active area of the second radiation detector 34. The collimator 36 can also control how the radiation beam 32 is positioned on the detector 34. In one embodiment, the collimator 36 could have one degree/dimension of motion (e.g., to make a thinner or fatter slit). In another embodiment, the collimator 36 can have two degrees/dimensions of motion (e.g., to make various sized rectangles). In other embodiments, the collimator 36 may be capable of various other dynamically-controlled shapes, including, for example, parallelograms. All of these shapes may be dynamically adjusted during a scan. In some embodiments, blocking portions of the collimator can be rotated and/or translated.

The collimator/beamformer 36 may be configured in a variety of ways that allow it to adjust the shape of the radiation beam 32 emitted by the second source of radiation 30. For example, the collimator 36 can be configured to include a set of jaws or other suitable members that define and selectively adjust the size of an aperture through which the radiation beam from the second source of radiation 30 may pass in a collimated manner. In accordance with one exemplary configuration, the collimator 36 can include an upper jaw and a lower jaw, where the upper and lower jaws are movable in different directions (e.g., parallel directions) to adjust the size of the aperture through which the radiation beam from the second source of radiation 30 passes, and also to adjust the beam 32 position relative to the patient to illuminate only the portion of the patient to be imaged for optimized imaging and minimized patient dose. For example, a collimator can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

In accordance with one embodiment, the shape of the radiation beam 32 from the second source of radiation 30 can be changed during an image acquisition. Stated differently, in accordance with one exemplary implementation, the collimator 36 leaf positions and/or aperture width can be adjusted before or during a scan. For example, in accordance with one embodiment, the collimator 36 can be selectively controlled and dynamically adjusted during rotation of the second source of radiation 30 such that the radiation beam 32 has a shape with sufficient primary/shadow regions and is adjusted to include only an object of interest during imaging (e.g., the prostate). The shape of the radiation beam 32 being emitted by the second source of radiation 30 can be selectively controlled during or after a scan, depending on the desired image acquisition, which may be based on imaging and/or therapeutic feedback, as discussed in more detail below.

It will be further appreciated that the first source of radiation 20 can include or otherwise be associated with a beamformer or collimator. The collimator/beamformer associated with the first source of radiation 20 can be configured in a number of ways, similar to the collimator 36 associated with the second source of radiation 30.

The collimator assembly 36 can be controlled to adjust the shape of the radiation beam 32 emitted by the second source of radiation 30 dynamically in a number of geometries, including, but not limited to, a fan beam, thick fan beam, or cone beam having a beam thickness (width) as low as one detector row width or including multiple detector rows, which may be only a portion of the detector's active area. In various embodiments, the thickness of the fan beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector 34 may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The collimator/beamformer 36 shape/position and detector 34 readout range can be controlled such that the radiation beam 32 from the x-ray source 30 covers as much or as little of the detector 34 based on the particular imaging task and scatter estimation process being carried out, including, for example, combinations of narrow and wide FOV scans. The device 10 has the ability to acquire both single rotation cone beam and wide and narrow beam angle cone beam images, helical or other.

In accordance with one exemplary embodiment, the radiotherapy device 10 has been described above as including a first source of radiation 20, a second source of radiation 30, a first radiation detector 24 positioned to receive radiation from the first source of radiation 20 and a second radiation detector 34 positioned to receive radiation from the second radiation source 30. It will be appreciated, however, that the radiotherapy device 10 can include a first source of radiation 20 (e.g., a source of therapeutic radiation), a second source of radiation 30 (e.g., a kV radiation source) and only a radiation detector 34 positioned to receive radiation from the second source of radiation 30 without departing from the scope of the disclosed technology.

The radiation source 20 may be mounted, configured, and/or moved into the same plane or a different plane (offset) than the radiation source 30. In some embodiments, scatter caused by simultaneous activation of the radiation sources 20, 30 may be incrementally reduced by offsetting the radiation planes. In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MV scatter on a kV detector.

Integrated as a radiotherapy device, apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, CBCT data, MRI data, PET data or 3D rotational angiography (3DRA) data, and/or any information obtained from these or other imaging modalities. In some embodiments, the device 10 can track in-treatment patient, target, or ROI motion.

A reconstruction processor 40 can be operatively coupled to the first detector 24 and/or second detector 34. In one embodiment, the reconstruction processor 40 is configured to generate patient images based on radiation received by detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The radiotherapy device 10 can include an operator/user interface 48, where an operator of the radiotherapy device 10 can interact with or otherwise control the radiotherapy device 10 to provide input relating to scan or imaging parameters and the like. The operator interface 48 can include any suitable input devices, such as a keyboard, mouse, voice-activated controller, or the like. The radiotherapy device 10 can also include a display 52 or other human-readable element to provide output to the operator of the radiotherapy device 10. For example, the display 52 can allow the operator to observe reconstructed patient images and other information, such as imaging or scan parameters, related to operation of the radiotherapy device 10.

It will be appreciated that the collimator assembly 36 positioned relative to the second source of radiation 30 can be configured to provide dynamic collimation of a radiation beam being emitted by the second radiation source 30.

The collimator assembly 36 can be controlled such that the beam 32 from the second radiation source 30 covers as much or as little of the second detector 34 based on the particular imaging task being carried out. For example, the collimator 36 can be selectively controlled to provide a fan beam having a fan thickness from a single detector row, which could be sub-millimeter, up to several centimeters, including, for example, a fan beam thickness of 3-4 centimeters (measured in the longitudinal direction in the detector plane). Such a beam configuration can be used in a continuous, helical fan-beam imaging mode in accordance with aspects of the disclosed technology. In accordance with another exemplary embodiment, the collimator 36 can be selectively controlled to provide a fan beam having a fan thickness of about one centimeter. In accordance with another exemplary embodiment, the collimator 36 can be selectively controlled to provide a fan beam having a fan thickness of more than one centimeter or several centimeters, including, for example, between about two centimeters and about four centimeters. In accordance with another exemplary embodiment, the collimator 36 can be selectively controlled to provide a beam 32 having a thickness between about fifteen centimeters and about thirty centimeters. In accordance with another exemplary embodiment, the collimator 36 can be selectively controlled to provide a beam 32 having a thickness between about thirty-five centimeters and about forty centimeters. Generally, the fan beam geometry can be controlled to yield fan beams that are thin (e.g., single row), thick (e.g., multi-row), or cone-shaped.

In addition to the above-described fan-beam collimation, it will be appreciated that the collimator 36 can be selectively controlled to provide other beam 32 geometries without departing from the scope of the disclosed technology. For example, the collimator 36 can be selectively controlled to provide a rectangular or substantially rectangular beam geometry covering only all or a part of an object of interest within a patient supported on the patient support.

In accordance with one implementation, the geometry of the beam 32 from the second radiation source 30 can be changed during an image acquisition. Stated differently, in accordance with one exemplary implementation, the collimator 36 leaf positions and/or aperture width can be adjusted before or during a scan. For example, in accordance with one implementation, the collimator 36 can be selectively controlled and dynamically adjusted during rotation of the second radiation source 30 such that the beam 32 has a rectangular geometry that includes only an object of interest during imaging (e.g., the prostate).

As shown in FIG. 2, the radiotherapy device 10 includes a controller (indicated generally as 60) operatively coupled to one or more components of the radiotherapy system 10. The controller 60 controls the overall functioning and operation of the radiotherapy device 10, including providing power and timing signals to the first radiation source 20 and/or the second radiation source 30 and a gantry motor controller that controls rotational speed and position of the rotatable gantry 12. It will be appreciated that the controller 60 can encompass one or more of the following: a patient support controller, a gantry controller, a controller coupled to the first radiation source 20 and/or the second radiation source 30, a collimator assembly controller, a controller coupled to the first detector 24 and/or the second detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The radiotherapy system 10 may include various components, logic, and software. In one embodiment, the controller 60 comprises a processor, a memory, and software. By way of example and not limitation, a radiotherapy system (such as, for example, radiotherapy system 10 shown in FIGS. 1 and 2) can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Other routines include processes and/or algorithms associated with data and image processing, including, for example, the processes described below. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with a radiotherapy device 10 can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with radiotherapy device 10.

Radiotherapy device 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The first source of radiation 20 and/or second source of radiation 30 can be operatively coupled to a controller 60 configured to control the relative operation of the first source of radiation 20 and the second source of radiation 30. For example, the second source of radiation 30 can be controlled and operated simultaneously with the first source of the radiation 20. In addition, or alternatively, the second source of radiation 30 can be controlled and operated sequentially with the first source of radiation 20, depending on the particular treatment and imaging plan being implemented.

It will be appreciated that the second detector 34 can take on a number of configurations without departing from the scope of the disclosed technology. As illustrated in FIG. 2, the second detector 34 can be configured as a flat-panel detector (e.g., a multi-row flat panel detector). In accordance with another exemplary embodiment, the second detector 34 can be configured as a curved detector.

Regardless of the configuration or geometry of the second detector 34, it will be appreciated that the collimator assembly 36 positioned relative to or otherwise associated with the second source of radiation 30 can be selectively controlled to control the shape of the radiation beam 32 emitted by the second radiation source 30 to selectively expose part or all of the second radiation detector 34. For example, in accordance with one exemplary embodiment, the beam from the second source of radiation can be collimated or otherwise controlled to provide a fan beam of imaging radiation. It will be appreciated that the size and geometry of the fan beam can be controlled based on the particular desired imaging application. In accordance with one example of the disclosed technology, the collimator assembly 36 can be selectively controlled such that the radiation beam 32 emitted by the second source of radiation is a fan beam, having a fan beam thickness greater than and down to about one centimeter. As discussed above, the geometry of the radiation beam 32 being emitted by the second radiation source can be changed during or after a scan, depending on the desired image acquisition, which may be based on imaging and/or therapeutic feedback, as discussed in more detail below.

Figure 3:
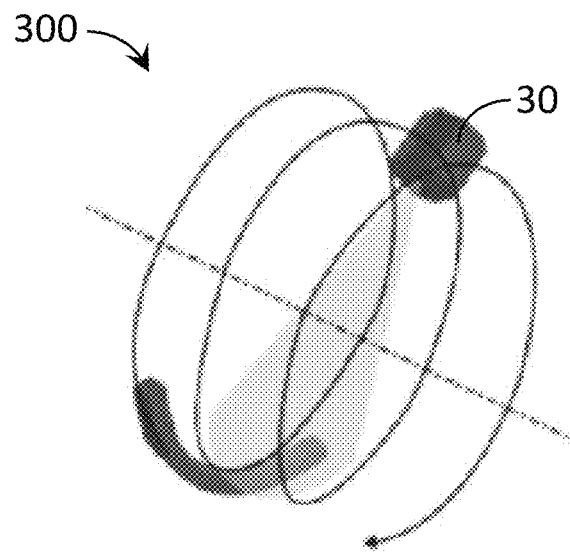
FIG. 3 is a diagrammatic illustration of an exemplary helical fan-beam radiation source trajectory used in connection with aspects of the disclosed technology.

It will be appreciated that the second source of radiation 30 and the second detector 34 positioned to receive radiation from the second source of radiation 30 can be configured to provide continuous rotation around the patient during an imaging scan. Further, synchronizing the motion and exposure of the second radiation source 30 with the longitudinal motion of the patient support can provide a continuous helical fan beam acquisition of a patient image during a procedure. FIG. 3 provides an exemplary diagrammatic illustration of a helical fan-beam source trajectory 300. In this embodiment, to achieve a helical trajectory, continuous circular rotation of the radiation source 30 is combined with longitudinal movement of the patient.

Figure 4:
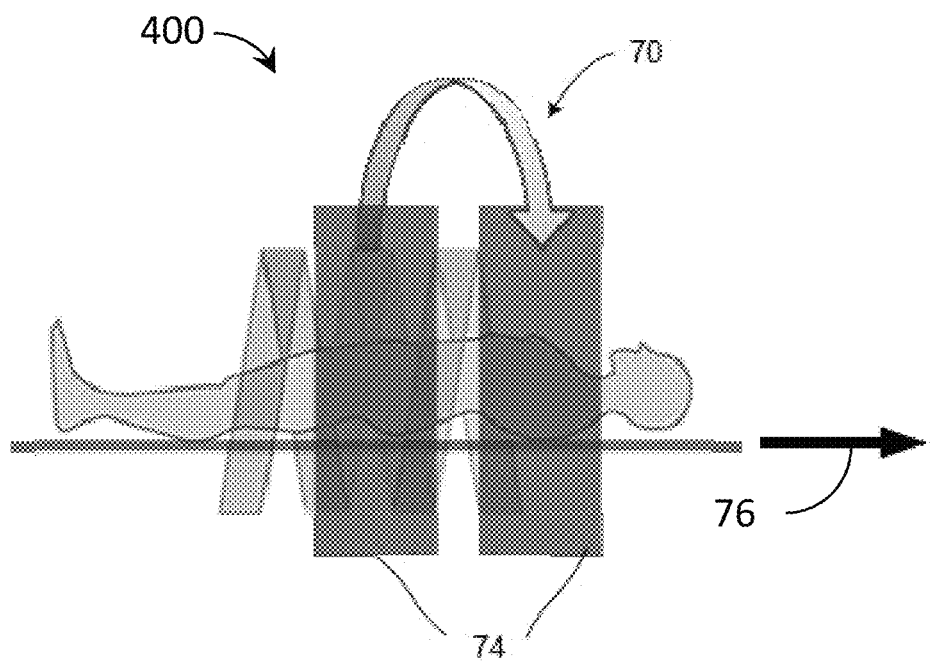
FIG. 4 is a diagrammatic illustration of an exemplary helical fan-beam radiation source trajectory and collimation used in connection with aspects of the disclosed technology.

In addition, FIG. 4 provides an exemplary diagrammatic illustration of a helical fan-beam image acquisition 400. The motion of the second radiation source 30 is indicated generally at 70, the collimator 36 leaves are schematically indicated generally at 74 by showing an exemplary fan beam column/slice width, and the patient support motion is indicated generally by the arrow 76 shown in FIG. 4.

It will be appreciated that radiation sources 20, 30 and detector(s) 24, 34 can be configured to provide rotation around the patient during an imaging and/or treatment scan in a number of ways. In one embodiment, synchronizing the motion and exposure of the source 20, 30 with the longitudinal motion of the patient support 18 can provide a continuous helical acquisition or scan of a patient image during a procedure. In addition to continuous rotation of the radiation sources 20, 30 and detector(s) 24, 34 (e.g., continuous and constant rotation of the gantry with constant patient motion speed and a constant collimator aperture), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The device 10 is capable of volume-based and planar-based imaging acquisitions. For example, in various embodiments, the device 10 may be used to acquire volume images and/or planar images and execute the associated processing, including scatter estimation/correction methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of device 10 described above.

In one embodiment, the aperture of the collimator 36 is set to a slit, such that it collimates the imaging radiation to a fan beam, the gantry 12 rotates continuously while moving the patient, to continuously collect collimated image data of the patient, such that the images are acquired in a helical fashion, and to reconstruct the images to generate a volume kV image.

In one embodiment, the gantry 12 rotation speed, the patient support 18 speed, the collimator shape, and/or the detector readout could all be constant during image acquisition. In other embodiments, one or more of these variables could change dynamically during image acquisition and/or treatment. The gantry 12 rotation speed, patient support 18 speed, collimator shape, and/or detector readout can be varied to balance different factors, including, for example, image quality, image acquisition time, dosage, workflow, etc.

An advantage of dynamic collimation (e.g., versus a fixed slit aperture) is that the imaging system can be used to acquire two-dimensional images (e.g., for motion tracking uses) and/or for a CBCT image (e.g., with one rotation, no patient motion, and no aperture collimation).

In another embodiment, the aperture of the collimator 36 can be used to form rectangular beams, which could be used, for example, to collimate the beam 32 to include only the object or region of interest. In this embodiment, the collimator 36 would change dynamically with rotation to keep the beam collimated to the target or region of interest (ROI).

In other embodiments, these features can be combined with one or more other image-based activities or procedures, including, for example, patient set up, adaptive therapy monitoring, treatment planning, etc.)

Figure 5:
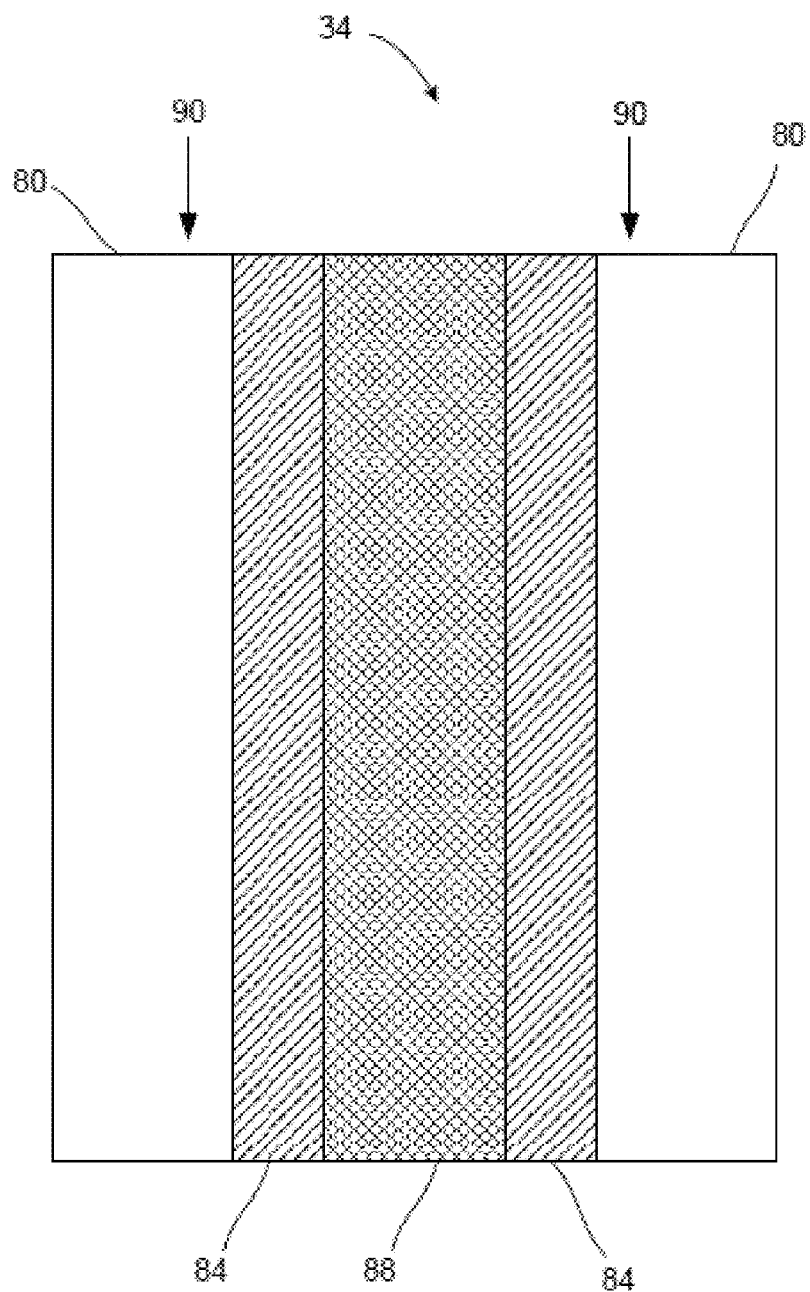
FIG. 5 is a diagrammatic illustration showing an exemplary detector where only a portion of the active area is exposed to radiation from the second radiation source in accordance with an exemplary aspect of the disclosed technology.

FIG. 5 is diagrammatic illustration of an exemplary embodiment of the second radiation detector 34 (e.g., a flat-panel detector) having an active region or area 80 positioned to detect or otherwise receive radiation from the second radiation source 30. In the illustrated exemplary embodiment, the active area 80 is larger than an area corresponding to projections 88 from the second radiation source 30. FIG. 5 is provided to illustrate selective control or collimation of the radiation emitted by the second radiation source 30 such that the geometry of the radiation emitted 32 covers less (and possibly significantly less) than the active area 80 of the associated detector 34. One exemplary beam geometry is a fan-beam geometry (e.g., where the fan beam is controlled or otherwise collimated to cover an area down to about one centimeter of the second radiation detector in the longitudinal direction). The illustrated embodiment can also be thought of as representing a multi-row detector, where the radiation beam 32 from the second radiation source 30 is collimated in the longitudinal direction to cover only a single detector row.

As can be seen in FIG. 5, making use of less than the entire active area 80 of the detector 34 allows for detection of radiation outside the area of the collimated beam 88 from the second radiation source 30. For example, the detector can receive penumbra (indicated generally as 84) from the second radiation source 30 and shadow region edges of the projection information from the second radiation source 30.

In this configuration, it is also possible to obtain an estimate of scatter from the scattered radiation (indicated generally by arrows 90 outside of the penumbra area) from the second source of radiation 30. In this manner, sections of the detector not exposed by the radiation source 30 can be used to assess the scatter radiation generated by the patient from the source 30 by interpolating the contamination in the beam (fan) from the detector response in the scatter region or area 90 on either side of the projection information 88 (and penumbra 84). In addition, it will be appreciated that in the fan beam geometry, sections of the detector 34 not exposed by the second radiation source 30 (e.g., kV source) can also be used to assess the residual effect of the scatter from the first radiation source 20 (e.g., MV source) when the two sources 20, 30 are operated simultaneously. As mentioned above, in one embodiment, area 88 (with penumbra 84) may be 3-4 centimeters wide within a 5-6 centimeter detector 80. Various other exposed and active area sizes or ratios of exposed-to-active detector area may be used in other embodiments.

In the illustrated embodiment, the second source of radiation 30 and the associated second detector 34 are positioned approximately 180 degrees from one another about the rotating gantry 12. It will be appreciated that the second source of radiation 30 and the associated second detector 34 can be positioned in different orientations than 180 degrees offset. For example, the second radiation source 30 and the associated second detector 34 can be positioned relative to one another to achieve a half-fan CT acquisition.

As is discussed above, aspects of the disclosed technology can be utilized by a radiotherapy device and methods that make use of integrated lower energy (e.g., kV) CT for use in conjunction with or as part of IGRT. In accordance with one embodiment, the image acquisition methodology can include or otherwise makes use of a helical source trajectory (e.g., a continuous source rotation about a central axis together with longitudinal movement of a patient support through a gantry bore) with a fan or "thick-fan" beam collimation, together with fast slip ring rotation, for example, to provide kV CT imaging on a radiation therapy delivery platform. It will be appreciated that such an implementation can provide reduced scatter and improved scatter estimation to enable kV images of higher quality than conventional systems.

In some embodiments, it will be appreciated that any potential increased scan time associated with multiple fan-beam rotations to complete a volume image can be mitigated or otherwise offset by high kV frame rates, high gantry rates, and/or sparse data reconstruction techniques. It will be further appreciated that the above-described provision of a selectively controllable collimator allows for a system where a user can trade off or otherwise vary image acquisition time versus image quality, depending on the specific application and/or clinical need. It also will be appreciated that the radiotherapy delivery device can be controlled to provide half- or single-rotation cone beam CT scans (with potential reduced image quality due to scatter) with fast image acquisition time (e.g., for motion tracking), as well as circular or continuous helical acquisition with a narrow/slit fan beam with longer acquisition time, but increased image quality due to reduced scatter.

The following flow charts and block diagrams illustrate exemplary configurations and methodologies associated with IGRT in accordance with the systems described above. The exemplary methodologies may be carried out in logic, software, hardware, or combinations thereof. In addition, although the procedures and methods are presented in an order, the blocks may be performed in different orders, including series and/or parallel. In particular, for example, the first and second radiation sources 20, 30 may be activated sequentially and/or simultaneously. Thus, the steps below, including imaging, image-based pre-delivery steps, and treatment delivery, although shown sequentially, may be executed simultaneously, including in real-time. Further, additional steps or fewer steps may be used.

Figure 6:
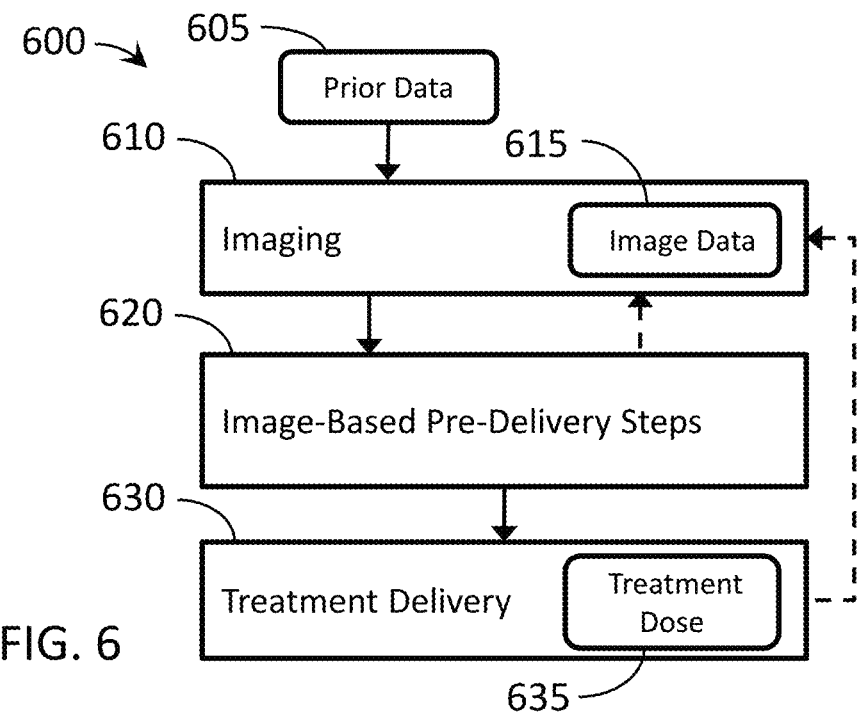
FIG. 6 is a flow chart depicting an exemplary method of IGRT using a radiotherapy device.

FIG. 6 is a flow chart depicting an exemplary method 600 of IGRT using a radiotherapy device (e.g., radiotherapy device 10). Prior data 605 can include images of the patient (e.g., a prior image, which may be a previously-acquired planning image, including a prior CT image), treatment plans, phantom information, models, a priori information, etc. In some embodiments, the prior data 605 is generated by the same radiotherapy device, but at an earlier time. At step 610, imaging of a patient is performed using a source of low-energy radiation (e.g., kV radiation from second radiation source 30). In one embodiment, imaging comprises a helical scan with a fan beam geometry. Step 610 can produce high-quality (HQ) image(s) or imaging/scan data 615 using the techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 610 can also include image processing to generate patient images based on the imaging/scan data 615 (e.g., in accordance with methods described above). In some embodiments image processing is a separate step, including where image processing is executed by separate devices.

Next, at step 620, one or more image-based pre-delivery steps, discussed below, are performed based at least in part on the imaging data 615 from step 610. As discussed in more detail below, step 620 can include determining various parameters associated with the therapeutic treatment and (subsequent) imaging planning. In some embodiments, image-based pre-delivery steps (620) may require more imaging (610) before treatment delivery (630). Step 620 can include adapting a treatment plan based on the imaging data 615 as part of an adaptive radiotherapy routine. In some embodiments, image-based pre-delivery steps 620 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 630, therapeutic treatment delivery is performed using a source of high-energy radiation (e.g., MV radiation from first radiation source 20). Step 630 delivers a treatment dose 635 to the patient according to the treatment plan. In some embodiments, the IGRT method 600 may include returning to step 610 for additional imaging at various intervals, followed by image-based pre-delivery steps (620) and/or treatment delivery (630) as required. In this manner the high quality imaging data 615 may be produced and utilized during IGRT using one radiotherapy device 10 that is capable of adaptive therapy. As mentioned above, steps 610, 620, and/or 630 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 7:
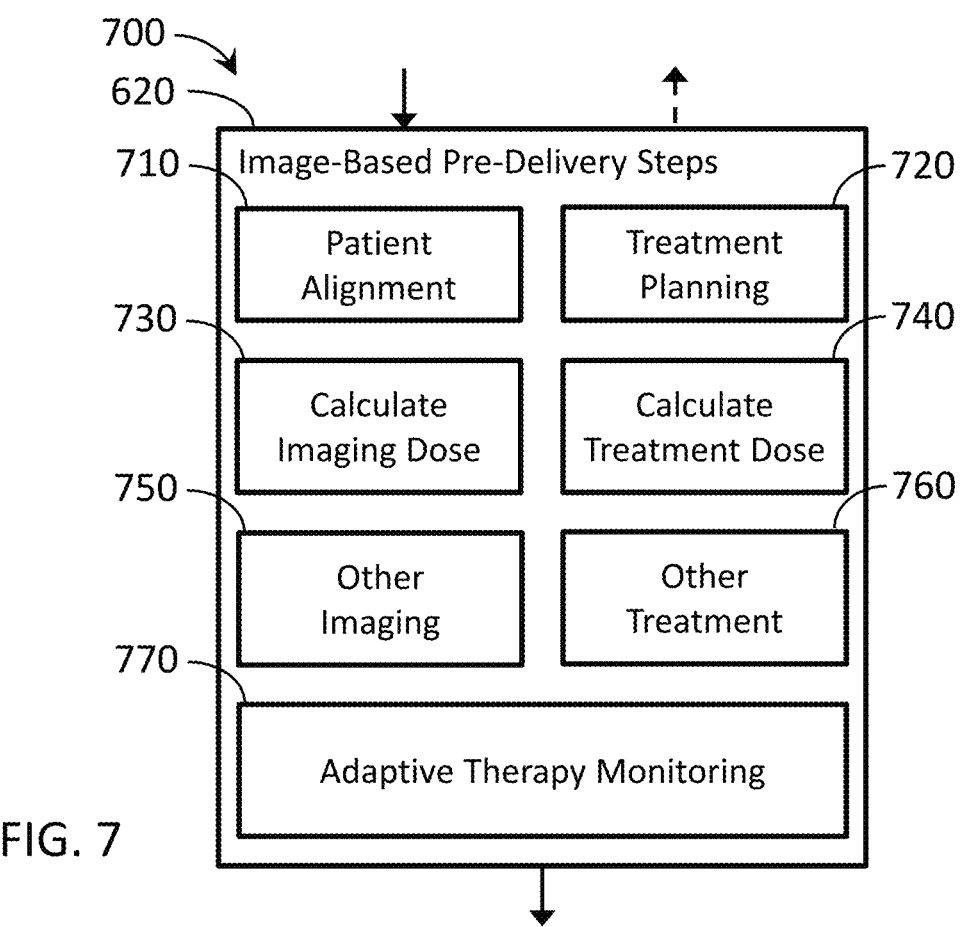
FIG. 7 is a block diagram depicting exemplary image-based pre-delivery steps.

FIG. 7 is a block diagram 700 depicting exemplary image-based pre-delivery steps/options that may be associated with step 620 above. It will be appreciated that the above-described radiotherapy device (e.g., radiotherapy device 10) can generate kV images that can be used in a variety of ways, including for image-based pre-delivery steps (620), without departing from the scope of the present invention. For example, images 615 generated by the radiotherapy device can be used to align a patient prior to treatment (710). Patient alignment can include correlating or registering the current imaging data 615 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the radiotherapy device can also be used for treatment planning or re-planning (720). In various embodiments, step 720 can include confirming the treatment plan, modifying the treatment plan, generating a new treatment plan, and/or choosing a treatment plan from a set of treatment plans (sometimes referred to as "plan of the day"). For example, if the imaging data 615 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 615 (generated by the radiotherapy device 10 at step 610), the imaging data 615 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the radiotherapy device 10 can be used to calculate imaging dose (730), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the radiotherapy device 10 can be used to calculate treatment dose (740), which may be used for ongoing determinations of total dose to the patient and/or may be included as part of treatment planning or re-planning.

In accordance with other exemplary use cases, images generated by the radiotherapy device 10 can be used in connection with planning or adjusting other imaging (750) and/or other treatment (760) parameters or plans, including, for example, as part of adaptive therapy and/or treatment plan generation. In accordance with another exemplary use case, images generated by the radiotherapy device 10 can be used in connection with adaptive therapy monitoring (770), which can include monitoring treatment delivery and adapting as required.

It should be appreciated that the image-based pre-delivery steps (620) are not mutually exclusive. For example, in various embodiments, calculate treatment dose (740) can be a step by itself and/or can be part of adaptive therapy monitoring (770) and/or treatment planning (720). In various embodiments, the image-based pre-delivery steps (620) can be performed automatically and/or manually with human involvement.

The devices and methods described above, including the collimation of the image radiation and the image radiation detector scheme, can provide reduced scatter and improved scatter estimation, which can result in kV-generated images of higher quality than conventional in-treatment imaging systems like CBCT.

As described above and with reference again to FIG. 5, the second source of radiation 30 may be controlled and/or collimated (e.g., by collimator 36) into a fan beam such that the imaging beam 32 does not directly expose the entire active area 80 of the detector 34 and allows for detection of radiation outside the area of the collimated beam 88 (projection data), including the penumbra region 84 and/or the scatter region 90.

Figure 8:
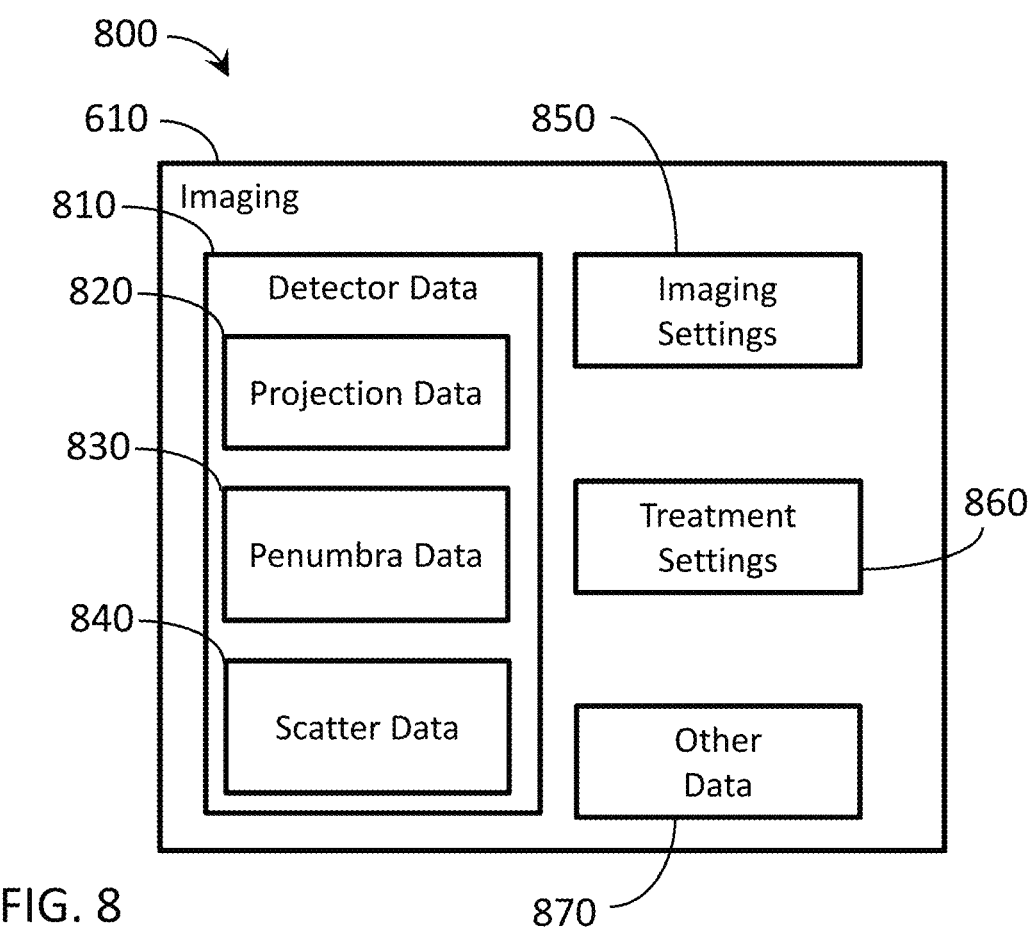
FIG. 8 is a block diagram depicting exemplary data sources that may be utilized during imaging or image-based pre-delivery steps.

FIG. 8 is a block diagram 800 depicting exemplary data sources that may be utilized during imaging (610) and/or subsequent treatment planning (620). Detector data 810 represents all of the data received by the image radiation detector 34. With continued additional reference to FIG. 5, the projection data 820 is the data generated by the radiation incident in the collimated beam area 88, which may be referred to as the primary region. The penumbra data 830 is the data generated by the radiation incident in the penumbra region or area 84. The scatter data 840 is the data generated by the radiation incident in the scatter (only) region or area 90.

In one embodiment, the penumbra data 830 may be used to separate or identify the projection and/or scatter data. In another embodiment, in a fan-beam geometry, the scatter data 840 can be used to determine the scatter radiation generated by the patient from the second radiation source 30 (e.g., kV) by interpolating the contamination in the projection data 820 from the scatter data 840. In another embodiment, also in a fan-beam geometry, the scatter data 840 can be used to determine the residual effect of the scatter from the first radiation source 20 (e.g., MV) when the two sources 20, 30 are operated simultaneously.

In this manner, the penumbra data 830 and/or the scatter data 840 may be utilized to improve the quality of the images generated by the imaging step 610. In some embodiments, the penumbra data 830 and/or the scatter data 840 may be combined with the projection data 820 and/or analyzed in view of the applicable imaging settings 850, treatment settings 860 (e.g., if simultaneous imaging and treatment radiation), and any other data 870 associated with the radiotherapy device 10 at the time of the data collection at the imaging detector 34. In other embodiments, the data may be used for the treatment planning step 620.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. A radiotherapy delivery device, comprising:
a rotatable gantry system positioned at least partially around a patient support;
a first radiation source coupled to the rotatable gantry system, the first radiation source configured for therapeutic radiation;
a second radiation source coupled to the rotatable gantry system, the second radiation source configured for imaging radiation, wherein the second radiation source comprises an energy level less than the first radiation source;
a radiation detector coupled to the rotatable gantry system and positioned to receive radiation from the second radiation source; and
a collimator assembly positioned relative to the second radiation source to selectively control a shape of a radiation beam emitted by the second radiation source to selectively expose a single, continuous area of the radiation detector to the radiation beam during a helical scan based on speed and image quality objectives.

2. The radiotherapy delivery device of claim 1, wherein the second radiation source comprises a kilovoltage (kV) radiation source.

3. The radiotherapy delivery device of claim 1, wherein the shape of the radiation beam is a fan beam.

4. The radiotherapy delivery device of claim 1, wherein the collimator assembly is selectively controlled to adjust the radiation beam during the helical scan.

5. The radiotherapy delivery device of claim 1, wherein the patient support moves at a variable speed relative to the rotatable gantry system.

6. The radiotherapy delivery device of claim 1, wherein the rotatable gantry system rotates around the patient support at a variable rate.

7. The radiotherapy delivery device of claim 1, wherein the second radiation source operates simultaneously with the first radiation source.

8. The radiotherapy delivery device of claim 1, wherein the second radiation source operates sequentially with the first radiation source.

9. The radiotherapy delivery device of claim 1, wherein an active area of the radiation detector comprises a penumbra region and a shadow region relative to the second radiation source.

10. The radiotherapy delivery device of claim 1, wherein an active area of the radiation detector acquires projection data from the second radiation source and scatter data from the first radiation source when the first radiation source and the second radiation source are operated simultaneously.

11. The radiotherapy delivery device of claim 1, further comprising a reconstruction processor, wherein the reconstruction processor generates patient images based on radiation received by the radiation detector.

12. A method of acquiring projection data from a radiotherapy device including a first radiation source configured for therapeutic radiation and a second radiation source configured for imaging radiation coupled to a rotatable gantry system, comprising:
controlling the second radiation source and a collimator assembly positioned relative to the second radiation source to provide a fan beam of radiation that exposes a single, continuous area of a radiation detector that is less than an active area of the radiation detector;
controlling the rotatable gantry system and a patient support to provide a helical scan of a patient on the patient support; and
providing imaging data from the active area of the radiation detector;
wherein controlling the second radiation source and the collimator assembly is based on speed and image quality objectives.

13. The method of claim 12, further comprising planning a therapeutic treatment based on the imaging data received by the radiation detector.

14. The method of claim 13, wherein planning the therapeutic treatment comprises at least one of aligning the patient, calculating an imaging dose, calculating a treatment dose, confirming a prior imaging data, confirming a prior treatment plan, generating a modified treatment plan, or generating a new treatment plan.

15. The method of claim 12, wherein radiation received by the radiation detector comprises projection data and penumbra data, and the method further comprises determining a scatter region based on the penumbra data.

16. The method of claim 12, wherein radiation received by the radiation detector comprises projection data and scatter data, and the method further comprises determining a patient scatter estimate due to the second radiation source based on the scatter data.

17. The method of claim 12, wherein the first radiation source and the second radiation source emit radiation simultaneously, and wherein radiation received by the radiation detector comprises projection data and scatter data, and the method further comprises determining a patient scatter estimate due to the first radiation source based on the scatter data.

18. The method of claim 12, further comprising generating patient images based on radiation received by the radiation detector from the second radiation source.

19. A radiotherapy delivery device, comprising:
a rotatable gantry system positioned at least partially around a patient support;
a first radiation source coupled to the rotatable gantry system, the first radiation source configured for therapeutic radiation;
a second radiation source coupled to the rotatable gantry system, the second radiation source configured for imaging radiation, wherein the second radiation source comprises an energy level less than the first radiation source;
a radiation detector coupled to the rotatable gantry system and positioned to receive radiation from the second radiation source;
a collimator assembly positioned relative to the second radiation source to selectively control a shape of a radiation beam emitted by the second radiation source to selectively expose a single, continuous area of the radiation detector to the radiation beam during a helical scan;
a data processing system configured to:
receive imaging data from an active area of the radiation detector; and
reconstruct an image of a patient based on the imaging data during IGRT;
wherein the collimator assembly selectively controls the shape of the radiation beam based on speed and image quality objectives.

* * * * *